US012447251B2

(12) United States Patent
Shashanka Jain et al.

(10) Patent No.: US 12,447,251 B2
(45) Date of Patent: Oct. 21, 2025

(54) PERITONEAL DIALYSIS USING PRESSURIZED CHAMBER

(71) Applicants: BAXTER INTERNATIONAL INC., Deerfield, IL (US); BAXTER HEALTHCARE SA, Glattpark (CH)

(72) Inventors: Belur Shanthakumar Shashanka Jain, Bangalore (IN); Anoop Thirumattathil Ashokan, Alappuzha Kerala (IN)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 435 days.

(21) Appl. No.: 17/927,141

(22) PCT Filed: May 25, 2021

(86) PCT No.: PCT/US2021/034062

§ 371 (c)(1),
(2) Date: Nov. 22, 2022

(87) PCT Pub. No.: WO2021/242762

PCT Pub. Date: Dec. 2, 2021

(65) Prior Publication Data

US 2023/0181804 A1 Jun. 15, 2023

(30) Foreign Application Priority Data

May 27, 2020 (IN) ............................ 202041022213

(51) Int. Cl.
*A61M 1/28* (2006.01)
*A61M 1/14* (2006.01)
*A61M 1/16* (2006.01)

(52) U.S. Cl.
CPC ................ *A61M 1/28* (2013.01); *A61M 1/14* (2013.01); *A61M 1/1601* (2014.02); *A61M 1/1654* (2013.01); *A61M 2205/3331* (2013.01)

(58) Field of Classification Search
CPC .... A61M 1/14; A61M 1/1601; A61M 1/1654; A61M 1/28; A61M 2205/3331
See application file for complete search history.

(56) References Cited

U.S. PATENT DOCUMENTS

| | | | |
|---|---|---|---|
| 6,488,647 B1 | 12/2002 | Hiromu et al. | |
| 2011/0160649 A1 | 6/2011 | Li | |
| 2016/0109421 A1 | 4/2016 | Bluchel et al. | |
| 2019/0344002 A1 | 11/2019 | McGill et al. | |

OTHER PUBLICATIONS

International Search Report—International Application No. PCT/US2021/034062 mailing date Sep. 21, 2021—6 pages.
Written Opinion—International Application No. PCT/US2021/034062 mailing date Sep. 21, 2021—7 pages.

*Primary Examiner* — John Kim
(74) *Attorney, Agent, or Firm* — K&L Gates LLP

(57) ABSTRACT

A peritoneal dialysis system and method includes a control unit configured to enable a pressurization device to pressurize a pressure cavity to a pressure; cause a fluid valve to be opened when the pressure reaches a desired pressure to allow fluid communication with a flexible container located within the pressure cavity; cause a pressure within the pressure cavity to be measured after the fluid valve is opened; and determine that the flexible container is full of fluid or empty of fluid if the pressure within the pressure cavity after the fluid valve is opened becomes or remains at least substantially constant.

15 Claims, 11 Drawing Sheets

PERITONEAL DIALYSIS USING PRESSURIZED CHAMBER

CROSS REFERENCE TO RELATED APPLICATIONS

The present application is a National Phase of International Application No. PCT/US2021/034062, filed May 25, 2021, which claims priority to and the benefit of Indian Application No. 202041022213, filed May 27, 2020, the entire contents of each of which are incorporated herein by reference in their entirety.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the peritoneal chamber, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a disposable set, which is discarded after a single use. Depending upon the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

There is also a need for APD devices to be portable so that a patient may bring his or her device on vacation or for work travel.

For each of the above reasons, it is desirable to provide a relatively simple, compact APD machine, which operates a simple and cost effective disposable set.

SUMMARY

The present disclosure relates to an automated peritoneal dialysis ("APD") machine or cycler, which uses a pressure chamber, which may be a rigid, e.g., clamshell, structure that accepts a disposable container, such as a disposable flexible container or bag. A lower or bottom portion of the pressure chamber may be fitted with a heating plate, e.g., a resistive heating plate, which heats the disposable bag during patient dwells and while it is filling and emptying fresh dialysis fluid. The rigid container may be made of plastic, such as, polyvinyl chloride ("PVC"), polyethylene ("PE") or polyurethane ("PU"), or of metal, such as stainless steel or aluminum. The rigid container may be reusable or disposable. The disposable bag is made of a medically safe material such as PVC or a non-PVC material. Where the chamber is a clamshell chamber, a seal such as an o-ring seal may be placed between the clamshell portions to seal same when closed together.

A fluid connection is made between the flexible container or bag and a tube or line extending outside of the pressure chamber. If the chamber is reusable, the chamber may be provided with a bulkhead connector having ports or fittings to which a disposable bag tube or pigtail is connected inside the chamber and to which an external tube or line is connected outside the chamber. In an alternative reusable chamber embodiment, the chamber defines a hole or aperture lined with a compressible material, wherein the tube or line from the flexible bag is extended in a sealed manner through the hole or aperture and is connected in a sterile manner outside the chamber to the supply and drain lines. In a further alternative reusable chamber embodiment, the disposable bag, the line extending from the bag and the solution and drain lines are provided as a premade and presterilized set, wherein the line extending from the bag is fitted, e.g., adhered, to a compressible seal, which is placed between the clamshells of the chamber for sealed operation.

In an embodiment, when the chamber is disposable, the disposable bag, the line extending from the bag, and the solution and drain lines are provided as a premade and presterilized set, wherein the line extending from the bag is permanently sealed to the disposable pressure chamber.

In one embodiment, the single line extending from the disposable flexible container or bag splits into multiple, e.g., five separate lines, each interfacing with a valve, such as an electrically actuated solenoid pinch valve, an electrically actuated motorized pinch valve or a pneumatically actuated valve. Heated, fresh dialysis fluid flows from the disposable bag to the patient through a patient line, while used dialysis fluid flows from the patient through the patient line to the disposable bag. Used dialysis fluid flows from the disposable bag to drain through a drain line. If an external heater is provided, fresh dialysis fluid flows from the disposable bag to a heater through a heater line, where it is heated, and then back to the disposable bag through the heater line. If the pressure chamber is reusable and provided with a heater, then the external heater line is not needed or may be used as a second fill line. Fresh dialysis fluid flows from supply and last fill containers through supply and last fill lines to the disposable bag before heating. Each of the patient line, drain line, heater line (if needed), supply line and last fill line are in fluid communication with the common line extending from the pressure chamber (and possibly extending from the disposable bag through the pressure chamber). Each of the fluid containers, including the flexible container or bag located within the pressure chamber and the fluid lines form a disposable set.

The pressure chamber is placed in pneumatic with a pressurization device, e.g., a motive fluid or air cylinder. A motive fluid or pneumatic valve is located between the cylinder and the pressure chamber. The motive fluid or pneumatic valve allows or disallows the flow of air to the pressure chamber and may be pneumatically or electromechanically actuated. In an embodiment, the motive fluid or pneumatic valve includes a three-way valve with one passage or port in communication with the pressure chamber, one passage or port in communication with a vent and a third passage or port in communication with the cylinder. The cylinder in an embodiment interfaces with a piston having a piston head, which is moved inside of the cylinder by a linear actuator, for example, a lead screw connected to a motor, e.g., a stepper motor. A feedback mechanism, e.g., a potentiometer or motor encoder, may be provided to track the location of the piston head and monitor its movement as it moves back and forth across the cylinder.

It should be appreciated that other types of pumping, alternative to a piston/cylinder may be used. For example, a volumetric pneumatic pump operating with a diaphragm or membrane may also be used to build positive and negative pressure. Another possible pump is a squirrel pump, which can likewise build positive and negative pressure. The alternative pumps may be able to build pressure more quickly.

The system operates using the pressurization device or cylinder to draw fluid from a desired source into the disposable flexible container or bag and then push the fluid out to a desired fluid destination. The desired fluid sources and destinations depend on the stage of treatment. The patient and the heater bag (if provided) may be either a source or a destination, the drain is (typically) only a destination, while the supply bag and last bag are (typically) only a source. In alternative embodiments, one or more supply bag may be used later in treatment as a drain bag to limit disposable waste and cost. Here, the supply and drain bag at different times are a source and a destination.

Each of the drawing-fluid-in and pushing-fluid-out sequences begins with building a pressure within the pressure chamber. Here, all fluid valves are closed and the pneumatic pressure chamber and vent passages or ports are alternated to build a desired starting pressure within pressure chamber (e.g., −1.5 psig for filling from the patient and +1.5 psig for pumping to the patient). To build negative pressure within the pressure chamber, the pressure chamber passage or port is closed and the vent port is opened when the piston head is extended within the cylinder to vent the air from the cylinder. Next, the vent port is closed and the pressure chamber port is opened while the piston head is retracted within the cylinder to build a certain amount of negative pressure in the pressure chamber as measured by a pressure sensor, which may be located between the pressurization device or cylinder and the motive fluid or pneumatic valve. The sequence just described is repeated until a desired amount of negative pressure is built within the pressure chamber (e.g., −1.5 psig). When the desired negative starting pressure is built, a desired liquid source valve is opened to let a desired fluid (e.g., patient effluent, heated fresh fluid, or supply fresh fluid) into the disposable flexible container or bag. The entire sequence just described is then repeated to rebuild the starting motive fluid or pneumatic pressure and to continue filling the disposable bag until there is no change in pressure as measured by the pressure sensor when the fluid valve is opened, indicating that the bag is full. That is, there is no more room within the disposable container or bag to relieve the vacuum.

To build positive pressure within the pressure chamber, the pressure chamber passage or port is closed and the vent port is opened, while the piston head is retracted within the cylinder to allow air to fill the cylinder through the vent. Next, the vent port is closed and the pressure chamber port is opened, while the piston head is extended within the cylinder to build a certain amount of positive pressure in the pressure chamber as measured by the pressure sensor. That sequence is repeated until a desired amount of positive pressure is built within the pressure chamber (e.g., +1.5 psig). When the desired positive starting pressure is built, a desired liquid destination valve is opened to expel a desired fluid (e.g., heated fresh, fresh supply or patient effluent) from the disposable flexible container or bag. The entire sequence just described is then repeated to rebuild starting motive fluid or pneumatic pressure and to continue expelling fluid from the disposable bag until there is no change in pressure when the fluid valve is opened as measured by the pressure sensor, indicating that the bag is empty. That is, there is no more room in the disposable container or bag to relieve the positive pressure.

It is contemplated during either or both of the negative and positive pressure sequences just described to rebuild the starting pressure and release the rebuilt pressure to the pressure chamber prior to the pressure chamber completely running out of driving pressure. Doing so results in a more continuous fluid flow.

To know how much fluid has been delivered to or from the disposable flexible container or bag, a rough estimate may be provided by a known volume of the disposable bag and assuming the bag is completely filled from empty to full or completely emptied from full to empty. A more precise calculation is performed by adding volumes calculated from the known piston head displacements associated with building and rebuilding the negative and positive pressures, knowing the volumetric dimensions of the pressurization device or cylinder, and assuming each of the fluids pumped to be incompressible.

A third option for volume control is to provide one or more load cell supporting the disposable container. Weight of fluid entering or leaving the container is converted to volume knowing the density of the fluid.

A control unit having one or more processing and memory is provided to control all of the fluid valves, all of the motive fluid or pneumatic valves, or each passage or port of a single three-way motive fluid valve, to read the output of the pressure sensor, to control the heater (provided within the pressure chamber or external to the pressure chamber), to control the linear actuator (e.g., stepper motor coupled to a lead or ball screw), to read the output from the potentiometer or motor encoder and calculate volume delivered, and to interface with a user interface. The user interface may be provided with a touchscreen and/or electromechanical push-buttons to allow the user or patient to enter parameters for treatment and a display screen for providing information, such as treatment status information.

As discussed in detail herein, the control unit is additionally programmed to handle a situation in which the container becomes completely empty prior to the full use of a positive pressure charge in the chamber. The control unit is also programmed to handle a situation in which the container becomes completely full prior to the full use of a negative pressure charge in the chamber. The control unit is further programmed to handle a situation in which the patient becomes empty during a patient drain prior to the full use of a negative pressure charge in the chamber.

Additionally, a continuous ambulatory peritoneal dialysis ("CAPD") system is disclosed herein, which employs the same type of pumping as the APD system. The CAPD system includes a pressure chamber in which a fresh supply container (e.g., bag) and a drain container (e.g., bag) are located in one embodiment. The piston, cylinder, motor, motor control devices, encoder or potentiometer, valve, filter and associated structure, functionality and alternatives discussed above for the APD system are likewise provided in the CAPD system. Additionally, temperature sensors and possibly an air heater may be provided with the CAPD system (with the APD system also) for increasing accuracy. A control unit is provided to run and receive signals from all above equipment and to perform patient drain and fill sequences in the same manner as described for the APD system. One difference in the CAPD system may be the provision and use of different fresh and drain bags within the chamber.

In light of the disclosure set forth herein, and without limiting the disclosure in any way, a peritoneal dialysis system includes: a pressure chamber; a disposable set including a flexible container located within the pressure chamber, at least one source line and at least one destination line; a motive fluid pressurization device; a motive fluid pressure sensor; and a control unit in operable communication with the motive fluid pressurization device and the motive fluid pressure sensor, the control unit configured to (i) pressurize the pressure chamber on the outside of the flexible container to a desired positive or negative motive fluid pressure used to push fluid out of the flexible container through one of the at least one destination line or pull fluid into the flexible container through one of the at least one source line, respectively, and (ii) repeat (i) until a motive fluid pressure read by the motive fluid pressure sensor becomes or remains at least substantially constant when it is attempted to push fluid out of the flexible container or pull fluid into the flexible container, indicating that the flexible container is empty or full, respectively.

In a second aspect, which may be combined with any other aspect described herein, the pressure chamber is reusable and is configured to open to accept the flexible container and to close to seal around a common line extending from the flexible container.

In a third aspect, which may be combined with any other aspect described herein, the pressure chamber is disposable and sealed to a common line extending from the flexible container.

In a fourth aspect, which may be combined with any other aspect described herein, the at least one source line includes at least one supply line connected to a supply of fresh peritoneal dialysis fluid and a patient line for removing used peritoneal dialysis fluid, and the at least one destination line includes the patient line for delivering fresh peritoneal dialysis fluid and a drain line for removing used peritoneal dialysis fluid.

In a fifth aspect, which may be combined with any other aspect described herein, the pressure chamber includes a fluid heater positioned to heat fluid within the flexible container.

In a sixth aspect, which may be combined with any other aspect described herein, the at least one source line and the at least one destination line include a heater line for extending to a heating container for heating fresh peritoneal dialysis fluid.

In a seventh aspect, which may be combined with any other aspect described herein, the motive fluid pressurization device includes a motive fluid cylinder, a piston located within the air cylinder, and a linear actuator configured to extend and retract the piston.

In an eighth aspect, which may be combined with any other aspect described herein, the peritoneal dialysis system includes at least one motive fluid valve for opening and closing a pressure chamber passage and a vent passage, and wherein during (i) and (ii) the control unit is configured to perform a negative pressure sequence in which (a) the pressure chamber passage is closed and the vent passage is opened while the piston is extended within the motive fluid cylinder to push motive fluid out of the cylinder, after which (b) the pressure chamber passage is opened and the vent passage is closed while the piston is retracted to pull motive fluid from the pressure chamber into the cylinder to increase the negative pressure within the pressure chamber.

In a ninth aspect, which may be combined with any other aspect described herein, the peritoneal dialysis system includes a fluid valve associated with each of the at least one source lines, and wherein the control unit is configured to open a desired one of the fluid valves when the desired negative motive fluid pressure is reached via the negative pressure sequence.

In a tenth aspect, which may be combined with any other aspect described herein, the fluid valve includes a source line pinch valve.

In an eleventh aspect, which may be combined with any other aspect described herein, the peritoneal dialysis system which includes at least one motive fluid valve for opening and closing a pressure chamber passage and a vent passage, and wherein during (i) and (ii) the control unit is configured to perform a positive pressure sequence in which (a) the pressure chamber passage is closed and the vent passage is opened while the piston is retracted within the motive fluid cylinder to pull motive fluid into the cylinder, after which (b) the pressure chamber passage is opened and the vent passage is closed while the piston is extended to push motive fluid from cylinder into the pressure chamber to increase the positive pressure within the pressure chamber.

In a twelfth aspect, which may be combined with any other aspect described herein, the peritoneal dialysis system includes a fluid valve associated with each of the at least one destination lines, and wherein the control unit is configured to open a desired one of the fluid valves when the desired positive motive fluid pressure is reached via the positive pressure sequence.

In a thirteenth aspect, which may be combined with any other aspect described herein, the fluid valve includes a destination line pinch valve.

In a fourteenth aspect, which may be combined with any other aspect described herein, the linear actuator includes a ball or lead screw driven by a motor under control of the control unit.

In a fifteenth aspect, which may be combined with any other aspect described herein, the peritoneal dialysis system includes a feedback mechanism outputting to the control unit to enable the control unit to determine how far the linear actuator has extended or retracted the piston.

In a sixteenth aspect, which may be combined with any other aspect described herein, a peritoneal dialysis fluid system includes: a pressure chamber; a flexible container located within the pressure chamber; a motive fluid cylinder, a piston located within the motive fluid cylinder, and a linear actuator configured to extend and retract the piston; at least one motive fluid valve for opening and closing a pressure chamber passage and a vent passage; and a control unit in operable communication with the linear actuator and the at least one motive fluid valve, the control unit configured to perform at least one of (i) a negative pressure sequence in which (a) the pressure chamber passage is closed and the vent passage is opened while the piston is extended within the motive fluid cylinder to push motive fluid out of the cylinder, after which (b) the pressure chamber passage is opened and the vent passage is closed while the piston is retracted to pull motive fluid from the pressure chamber into the cylinder to increase the negative pressure within the pressure chamber acting on the flexible container, or (ii) a positive pressure sequence in which (a) the pressure chamber passage is closed and the vent passage is opened while the piston is retracted within the motive fluid cylinder to pull motive fluid into the cylinder, after which (b) the pressure chamber passage is opened and the vent passage is closed while the piston is extended to push motive fluid from cylinder into the pressure chamber to increase the positive pressure within the pressure chamber acting on the flexible container.

In a seventeenth aspect, which may be combined with any other aspect described herein, the peritoneal dialysis fluid system includes a motive fluid pressure sensor in communication with the control unit to measure at least one of the increased negative or positive pressures.

In an eighteenth aspect, which may be combined with any other aspect described herein, the flexible container is part of a disposable set along with at least one source line and a at least one destination line, and wherein at least one of the negative pressure sequence builds negative pressure to pull fluid into the flexible container via one of the at least one source line or the positive pressure sequence builds positive pressure to push fluid out of the flexible container via one of the at least one destination line.

In a nineteenth aspect, which may be combined with any other aspect described herein, the linear actuator includes a ball or lead screw driven by a motor under control of the control unit.

In a twentieth aspect, which may be combined with any other aspect described herein, a peritoneal dialysis method includes: enabling a pressurization device to pressurize a pressure cavity to a pressure; opening a fluid valve when the pressure reaches a desired pressure to allow fluid communication with a flexible container located within the pressure cavity; measuring the pressure within the pressure cavity after the fluid valve is opened; and determining that the flexible container is full of fluid or empty of fluid if the pressure within the pressure cavity after the fluid valve is opened becomes or remains at least substantially constant.

In a twenty-first aspect, which may be combined with any other aspect described herein, the desired pressure is different for different fluid sources or fluid destinations.

In a twenty-second aspect, which may be combined with any other aspect described herein, the peritoneal dialysis method includes determining that the flexible container is full or empty if the pressure within the pressure cavity after the fluid valve is opened becomes or remains at least substantially constant prior to pressurization from the pressurization device being exhausted.

In a twenty-third aspect, any of the features, functionality and alternatives described in connection with any one or more of FIGS. 1 to 11 may be combined with any of the features, functionality and alternatives described in connection with any other of FIGS. 1 to 11.

It is accordingly an advantage of the present disclosure to provide a relatively volumetrically accurate automated peritoneal dialysis ("APD") cycler.

It is another advantage of the present disclosure to provide an APD cycler that achieves relatively precise pressure control.

It is a further advantage of the present disclosure to provide a relatively quiet APD cycler.

It is still another advantage of the present disclosure to provide an APD cycler in which self-compensates for sensor drift.

It is yet a further advantage of the present disclosure to provide an APD system that may use a same disposable item for both pumping and heating.

It is still a further advantage of the present disclosure to provide an APD system that is able to build motive fluid or pneumatic pressure in a relatively simple manner.

It is yet another advantage of the present disclosure to provide an APD system that employs a relatively low cost disposable set.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
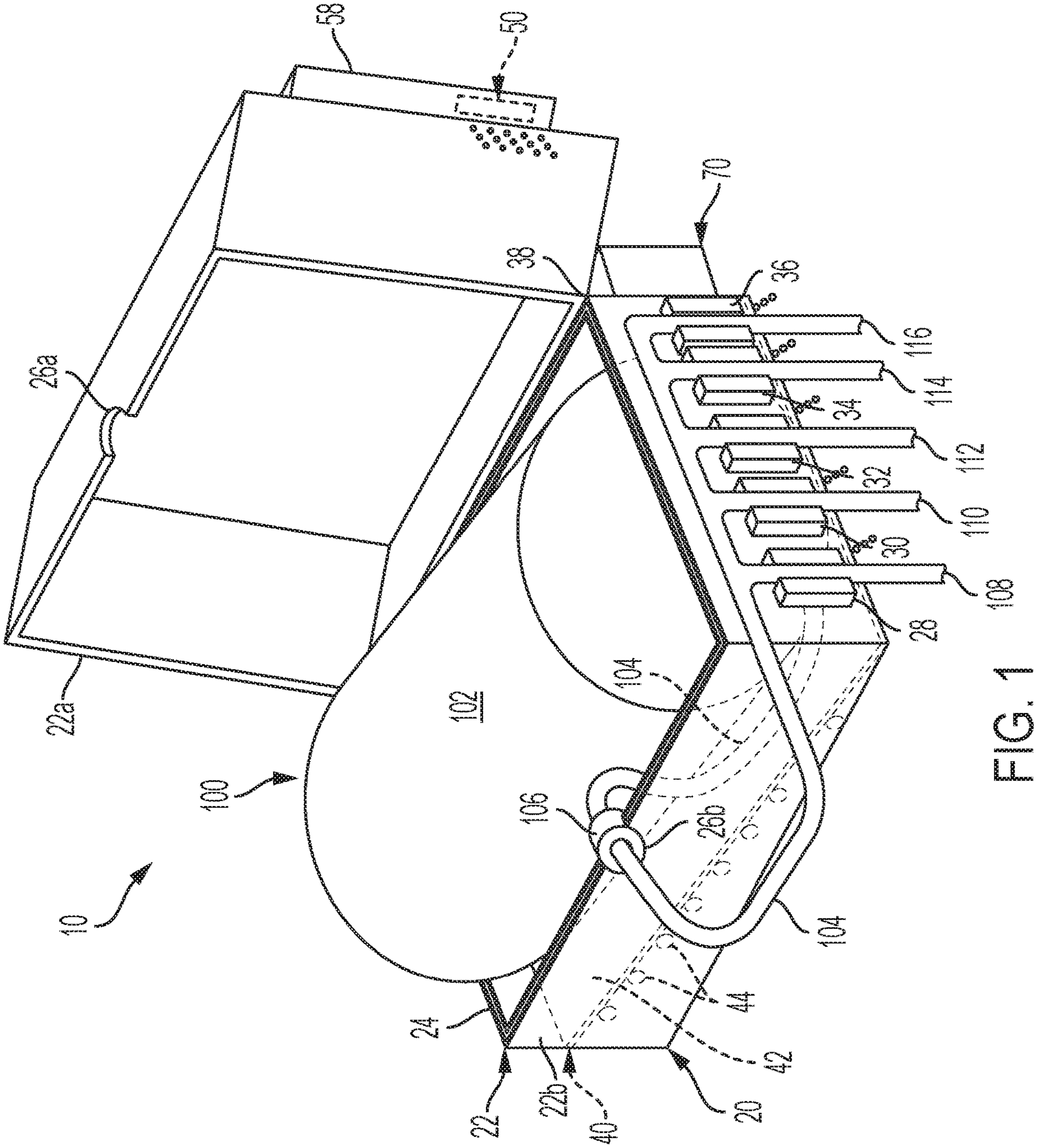
FIG. 1 is a perspective view of one embodiment of an automated peritoneal dialysis ("APD") cycler using pressurized chamber of the present disclosure.
Figure 2:
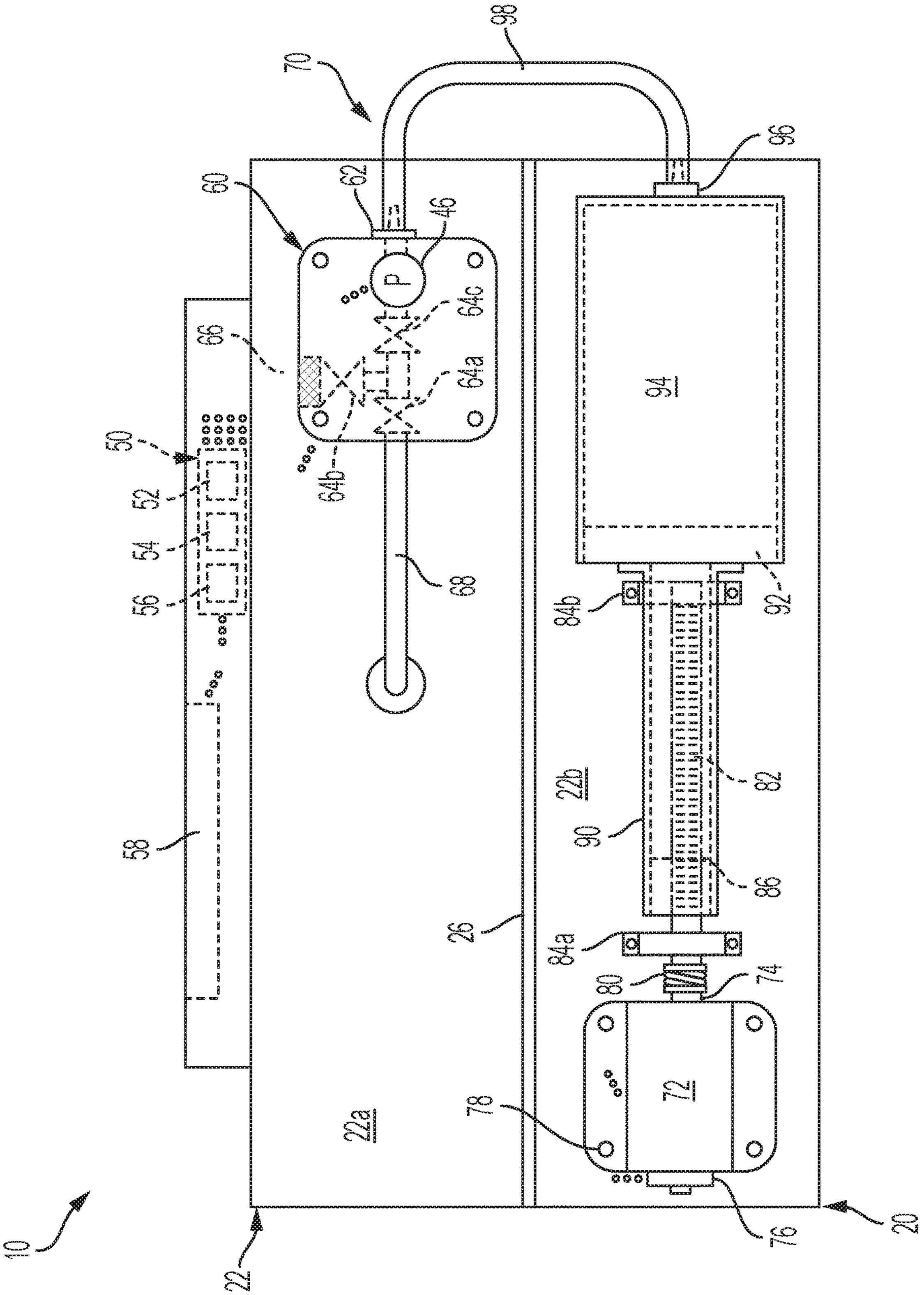
FIG. 2 is a rear view of one embodiment of an automated peritoneal dialysis ("APD") cycler using pressurized chamber of the present disclosure.

Referring now to the drawings and in particular to FIGS. 1 and 2, an automated peritoneal dialysis ("APD") system 10 includes and APD machine or cycler 20 that operates with a disposable set 100. APD machine or cycler 20 includes a housing 22 that defines a pressure chamber, which in the illustrated embodiment is a rigid, e.g., clamshell, structure that accepts a disposable container 102 of disposable set 100, such as a disposable flexible container or bag. Rigid container 22 may be made of plastic, such as, polyvinyl chloride ("PVC"), polyethylene ("PE") or polyurethane ("PU"), or of metal, such as stainless steel or aluminum. Rigid container 22 may be reusable or disposable. Disposable bag 102 is made of a medically safe material such as PVC or a non-PVC material. Where chamber 22 is a clamshell chamber, a seal such as an o-ring seal 24 (e.g., silicone) may be placed between the clamshell portions **22*a* and 22*b*** to seal same when closed together.

As illustrated in FIG. 1, a fluid connection is made between flexible container or bag 102 and a tube or line 104 extending outside of pressure chamber 22. If chamber 22 is reusable, the chamber may be provided with a bulkhead connector (not illustrated) having ports or fittings to which a disposable bag tube or pigtail is connected inside the chamber, wherein external tube or line 104 is connected to the bulkhead outside the chamber. In an alternative reusable chamber embodiment, chamber 22 defines a hole or aperture (not illustrated) lined with a compressible material, wherein tube or line 104 from flexible bag 102 is extended in a sealed manner through the hole or aperture and is connected in a sterile manner outside the chamber to the supply and drain lines. In a further alternative reusable chamber embodiment, which is illustrated in FIG. 1, disposable bag 102, line 104 extending from the bag, and the solution and drain lines are provided as a premade and presterilized set 100, wherein line 104 extending from the bag is fitted, e.g., adhered to a compressible seal 106, which is placed between correspondingly shaped cutouts **26*a* and 26*b* of clamshell halves 22*a* and 22*b*, respectively, of chamber 22** for sealed operation.

In an embodiment, when chamber 22 is disposable, disposable bag 102, line 104 extending from the bag, and the solution and drain lines are provided as a premade and presterilized set, wherein line 104 extending from bag 102 is permanently sealed to disposable pressure chamber 22. In a disposable arrangement, chamber 22 will not have the equipment connected to it as described below for the reusable version of chamber 22. The equipment is provided instead on a different housing (not illustrated). The equipment, however, may be at least substantially the same as described herein regardless of whether chamber 22 is reusable or disposable.

As illustrated in FIG. 1, single line 104 extending from the disposable flexible container or bag 104 splits into five separate lines 108, 110, 112, 114 and 116, each interfacing with a respective valve 28, 30, 32, 34 and 36, such as an electrically actuated solenoid pinch valve, an electrically actuated motorized pinch valve or a pneumatically actuated valve. Heated, fresh dialysis fluid flows from disposable container 102 to the patient through patient line 108, while used dialysis fluid flows from the patient through patient line 108 to disposable bag 102. Used dialysis fluid flows from disposable bag 102 to drain through drain line 110. If an external heater is provided, fresh dialysis fluid flows from disposable bag 102 to the external heater through heater line 112 to a heater bag (illustrated below), where it is heated, and then back to the disposable bag through heater line 112. If pressure chamber 22 is reusable and provided with a heater 40 discussed in more detail below, then external heater line 112 is not needed or is provided as an additional fresh dialysis fluid line. Fresh dialysis fluid flows from supply and last fill containers (illustrated below) through supply line 114 and last fill line 116 to disposable container 102 before heating. As illustrated, each of patient line 108, drain line 110, heater line 112 (if needed), supply line 114 and last fill line 116 are in fluid communication with common line 104 extending from pressure chamber 22 (and possibly extending from disposable container 102 through the pressure chamber). Each of the fluid containers, including flexible container or bag 102 located within pressure chamber 22 and fluid lines 104, 108, 110, 112, 114 and 116 form disposable set 100.

In FIG. 1, lower or bottom portion **22*b* of pressure chamber 22 is fitted with a heater plate 42, e.g., a resistive heating plate, as part of heater 40, which heats the fluid within disposable bag 102 while it is filling and emptying fresh dialysis fluid, and for subsequent fills, during patient dwell periods in which dialysis fluid resides in the patient's peritoneal cavity to perform treatment. Heater 40 in the illustrated embodiment includes resistive heating elements 44 through which current is passed to heat the elements and thus heater plate 42 and the fluid within container 102. Heater plate 42 in the illustrated embodiment is angled or tilted to force air towards an upper portion of container 102, while common line 104 extending through pressure chamber 22 extends in the other direction to connect to the lower end of container 102**.

FIGS. 1 and 2 illustrate that system 10 includes a control unit 50, which in the illustrated embodiment is provided with reusable pressure chamber 22, e.g., on the top of upper clamshell portion **22*a*. If pressure chamber 22 is disposable, control unit 50 is provided on an alternative APD machine housing (not illustrated). Control unit 50 is further alternatively provided as a wireless user interface, such as a tablet or smartphone. In any case, as illustrated in FIG. 2, control unit 50 may include one or more processor 52, one or more memory 54, and a video controller 56 interfacing with a user interface 58, which may include a display screen operating with a touchscreen and/or one or more electromechanical button, such as a membrane switch. User interface 58 may also include one or more speaker for outputting alarms, alerts and/or voice guidance commands. Control unit 50** may also include a transceiver and a wired or wireless connection to a network, e.g., the internet, for sending treatment data to and receiving prescription instructions from a doctor's or clinician's server interfacing with a doctor's or clinician's computer.

FIGS. 1 and 2 also illustrate that upper clamshell portion **22*a* and lower clamshell portion 22*b* may be connected via a hinge 38, which may be a living hinge or include separate hinges. Although not illustrated, one or more releasable locking mechanism may be provided to compress o-ring seal 24 when upper clamshell portion 22*a* is closed onto lower clamshell portion 22*b***.

FIGS. 1 and 2 also illustrate that pressure chamber 22 is placed in motive fluid or pneumatic communication with a pressurization assembly 70. Pressurization assembly 70 in the illustrated embodiment includes a motor 72, such as a stepper motor, having an output shaft 74, a feedback mechanism 76 such as an encoder, and mounting holes 78 for mounting motor to lower clamshell portion **22*b*. Output shaft 74 is coupled via a coupler 80 to a lead or ball screw 82 located behind a piston as described below. Coupler 80 may be a flexible couple configured to inhibit or reduce backlash, which increases positional accuracy. Lead or ball screw 82** may be provided with ball bearings to further prevent backlash and improve positional accuracy.

Lead or ball screw 82 is held between bearings **84*a* and 84*b*, which are mounted to lower clamshell portion 22*b*. A carriage 86 is threadingly engaged to lead or ball screw 82 and translates back and forth along lead or ball screw 82 depending on which direction it is turned by motor 72. Carriage 86 extends outwardly from lead or ball screw 82 to form one end of a piston 90 having a piston head 92, which is slidingly sealed within a motive fluid or air cylinder 94. In an embodiment, motor 72, lead or ball screw 82 and bearings 84*a* and 84*b* are metal, e.g., stainless steel, steel, aluminum and combinations and alloys thereof, while carriage 86, piston 90 and piston head 92** may be any of the metals listed or plastic, such as PVC, PE, PU, polycarbonate and combinations thereof. Each of those components is reusable in one embodiment.

FIG. 2 illustrates a state in which carriage 86, piston 90 and piston head 92 are in a fully retracted state relative to cylinder 94. If motor 72 is turned such that carriage 86 is translated to the right, piston 90 and piston head 92 will likewise extend within cylinder 94 to the right. Because piston head 92 is airtightly but slidingly sealed within cylinder 94, extending head 92 within cylinder 94 pushes a motive fluid, such as air, out of the cylinder via fitting 96. Fitting 96 in the illustrated embodiment is a hose barb fitting onto which a flexible motive fluid or pneumatic tube 98 is sealed. Flexible tube 98 may be made of any suitable material, such as PVC, PE, PU or silicone. The flexibility of tube 98 allows upper clamshell portion **22*a* to open relative to lower clamshell portion 22*b***.

FIG. 2 illustrates that the other end of motive fluid or pneumatic tube 98 is connected to a motive fluid or pneumatic valve 60 via a fitting 62, such as a hose barb onto which the flexible tube is sealed. Valve 60 is mounted to upper clamshell portion **22*a* and is located as illustrated between motive fluid or air cylinder 94 and pressure chamber 22. Motive fluid or pneumatic valve 60 allows or disallows the flow of motive fluid or air to pressure chamber 22 and may be pneumatically or electromechanically actuated. In the illustrated an embodiment, valve 60 includes a three-way valve with one passage or port 64*a* in motive fluid or pneumatic communication with pressure chamber 22, a second passage or port 64*b* in motive fluid or pneumatic communication with a reusable vent 66, such as a hydrophobic vent for filtering incoming air, and a third passage or port 64*c* in motive fluid or pneumatic communication with cylinder 94. In the illustrated embodiment, passage or port 64*a* is placed in motive fluid or pneumatic communication with pressure chamber 22 via line 68 (metal or plastic) fittingly connected to upper clamshell portion 22*a***.

FIG. 2 further illustrates that a pressure sensor 46 is located so as to sense a motive fluid or air pressure created via piston 90, piston head 92 and cylinder 94. Pressure sensor 46 in the illustrated embodiment is provided with valve 60 at a location between passage or port **64*c* and cylinder 94. Pressure sensor 46 may alternatively be located so as to operate with motive fluid or pneumatic tube 98 or to extend directly from cylinder 94**.

As illustrated in FIGS. 1 and 2, control unit 50 having one or more processing 52 and memory 54 is provided to control (as indicated by dotted control lines) all of fluid valves 28 to 36, at least one motive fluid or pneumatic valve 60 (e.g., each passage or port 64*a* to 64*c* of single three-way valve 60), to read the output of pressure sensor 46, to control heater 40 (provided within pressure chamber 22 or external to the pressure chamber), to control the linear actuator (e.g., stepper motor 72 coupled to lead or ball screw 82), to read the output from encoder 76 (or potentiometer as illustrated below) and calculate volume delivered, and to interface with user interface 58, which may be provided with a touchscreen and/or electromechanical pushbuttons to allow the user or patient to enter parameters for treatment and a display screen for providing information, such as treatment status information. Control unit 50 stores one or more program, and the processing to execute the one or more program, to operate each of the sequences discussed below.

Figure 3:
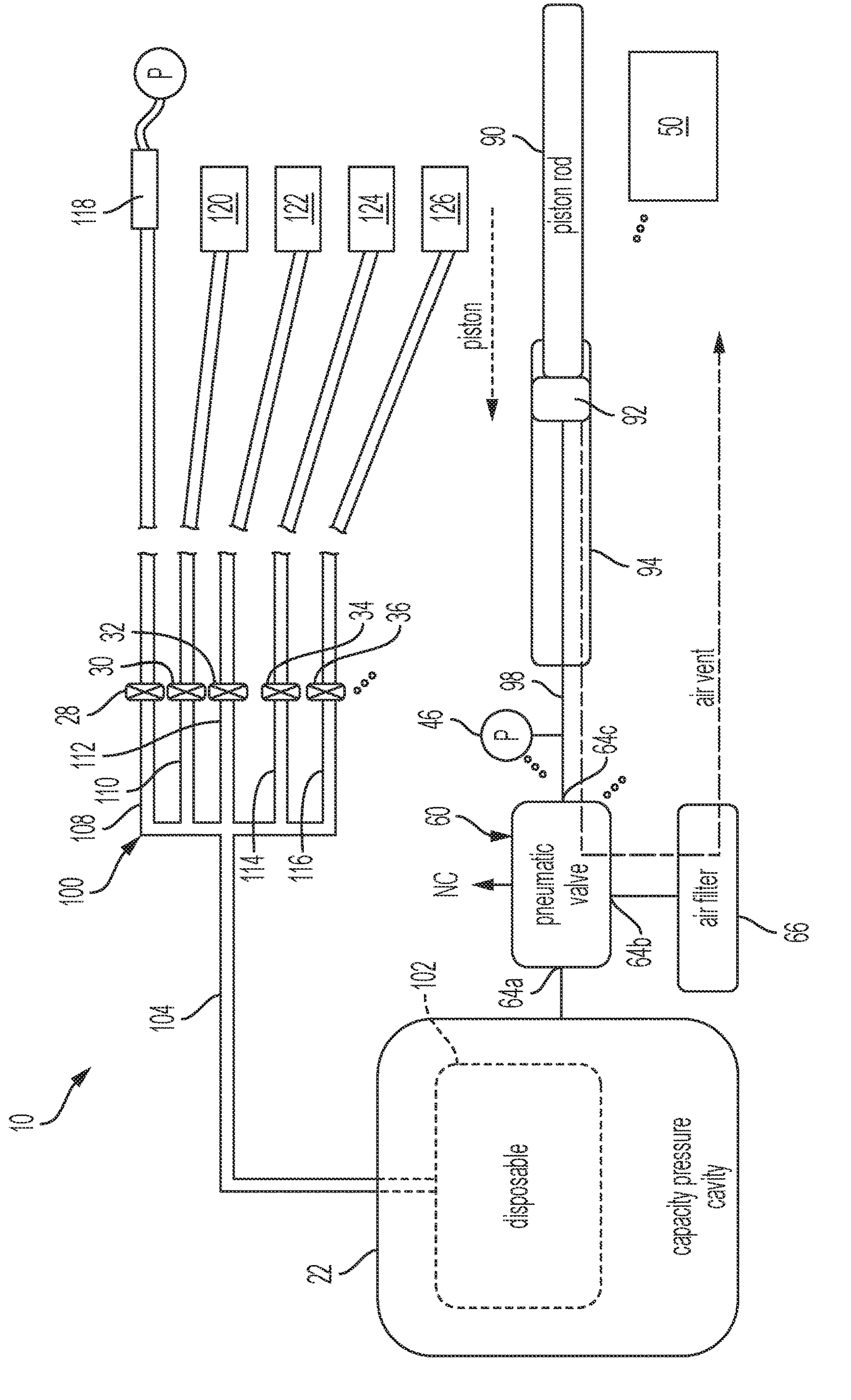
FIGS. 3 and 4 are schematic view illustrating a first step of one embodiment for a negative pressure sequence using the pressure chamber APD system of the present disclosure.

FIG. 3 illustrates that patient line 108 extends to a transfer set 118 for patient P. Disposable set 100 includes patient line 108 and a drain container or bag 120 connected to drain line 110 (drain line 110 alternatively extends to a house drain, e.g., a toilet or tub). Disposable set 100 further includes heater line 112 extending to heater container or bag 122 (heater 40 is alternatively provided within chamber 22), supply line 114 extending to supply container or bag 124 and last fill line 116 extending to last fill container or bag 126. System 10 operates using the pressurization assembly 70 including motive fluid or air cylinder 94 to draw fluid from a desired source into disposable flexible container or bag 102 and then push the fluid out to a desired fluid destination. The desired fluid sources and destinations depend on the stage of treatment. Patient P and heater bag 122 (if provided) may be either a source or a destination, drain bag 120 is (typically) only a destination, while supply bag 124 and last bag 126 are (typically) only sources. In alternative embodiments, one or more supply bag 124 may be used alternatively as a drain bag to limit disposable waste and cost. Here, the supply and drain bag at different times is a source and a destination.

In the methodology of system 10, each of the drawing-fluid-in and pushing-fluid-out sequences begins with building pressure (negative or positive) within pressure chamber 22. In the pressure building sequences, all fluid valves 28 to 36 are closed, while pressure chamber passage or port 64*a* and vent passage or port 64*b* are alternated (with cylinder passage or port 64*c* open) to build a desired starting pressure within pressure chamber 22. Desired starting pressures may include, for example, −1.5 psig for removing fluid from patient P, +1.5 psig for pumping fluid to patient P, and higher pressures, e.g., −3 to −5 psig for more quickly removing fluid from supply bag 124 and last fill bag 126 and, e.g., +3 to +5 psig for more quickly pumping fluid to drain bag 120 and heater bag 122 (if provided). It is accordingly contemplated that pressure chamber 22 and disposable container 102 be configured to withstand a pressure range, for example, −10 psig to +10 psig.

Figure 4:
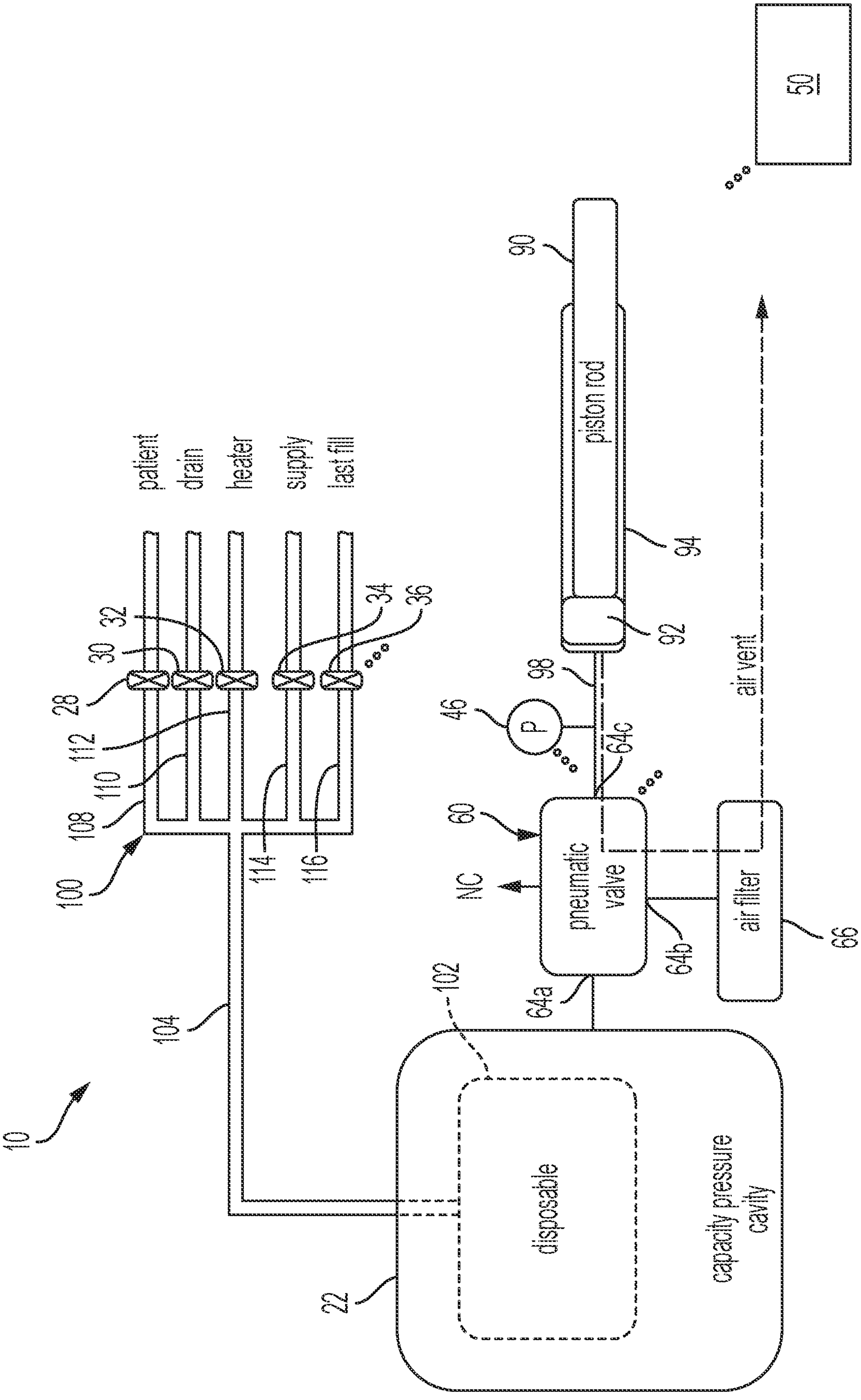

FIGS. 3 and 4 illustrate, via a piston arrow (dotted) and motive fluid arrow (dashed), that in a first step to build negative pressure within the pressure chamber 22, pressure chamber passage or port 64*a* is closed, while vent passage or port 64*b* and cylinder passage or port 64*c* are opened. Piston 90 and head 92 are extended (from FIG. 3 to FIG. 4) within cylinder 94 to vent air from the cylinder via vent 66. All fluid valves 28 to 36 are closed.

Figure 5:
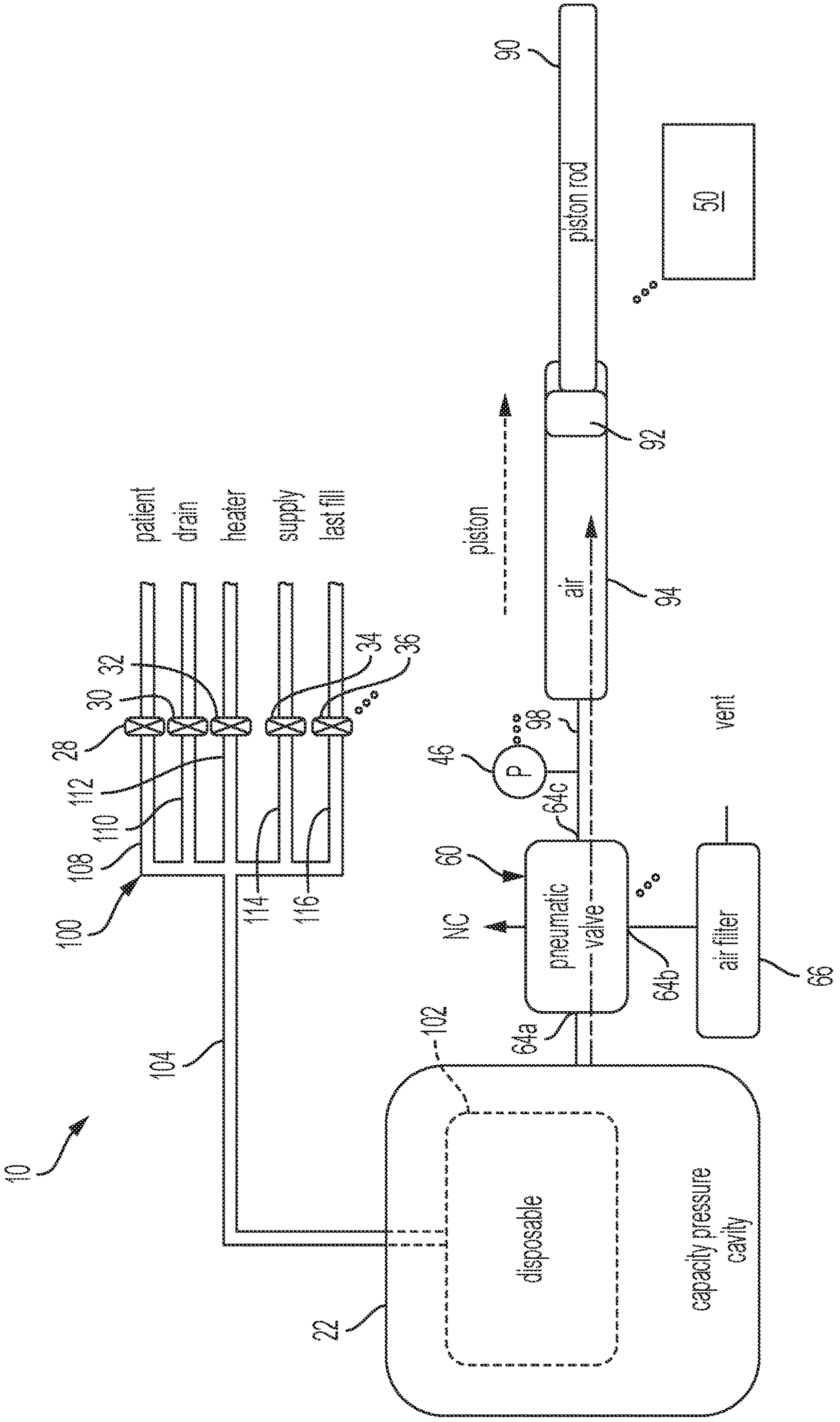
FIG. 5 is a schematic view illustrating a second step of one embodiment for a negative pressure sequence using the pressure chamber APD system of the present disclosure.

FIG. 5 illustrates, via the piston arrow and motive fluid arrow, that next, vent passage or port 64*a* is closed, while pressure chamber passage or port 64*b* and cylinder passage or port 64*c* are opened. Piston 90 and head 92 are retracted within cylinder 94 to build a certain amount of negative pressure in pressure chamber 22 as measured by pressure sensor 46, which here is located along motive fluid or pneumatic tube 98 between cylinder 94 and motive fluid or pneumatic valve 60. All fluid valves 28 to 36 remain closed.

The sequence just described between FIGS. 3 and 4 versus FIG. 5 is repeated until a desired amount of negative pressure is built within the pressure chamber 22 (e.g., −1.5 psig) as measured by pressure sensor 46. When the desired negative starting pressure is built, a desired liquid source valve is opened to let a desired fluid (e.g., patient effluent via fluid valve 28, heated fresh fluid via heater valve 32, or supply fresh fluid via valves 34 or 36) into disposable flexible container or bag 102. The negative pressure in chamber 22 is relieved via the expansion of container or bag 102. The fluid valve is closed when pressure sensor 46, with passages or ports 64*a* and 64*c* opened and vent passage or port 64*b* closed, detects that the pressure has returned to 0 psig.

The entire container 102 filling sequence just described, including the sequence described between FIGS. 3 and 4 versus FIG. 5, and the fluid valve opening and closing of the previous paragraph, is then repeated to rebuild the starting negative pressure and to continue filling disposable container or bag 102, until there is no change in pressure as measured by pressure sensor 46 when the desired fluid valve is opened, indicating that container or bag 102 is full. That is, there is no more room within container or bag 102 to relieve the vacuum.

Figure 6:
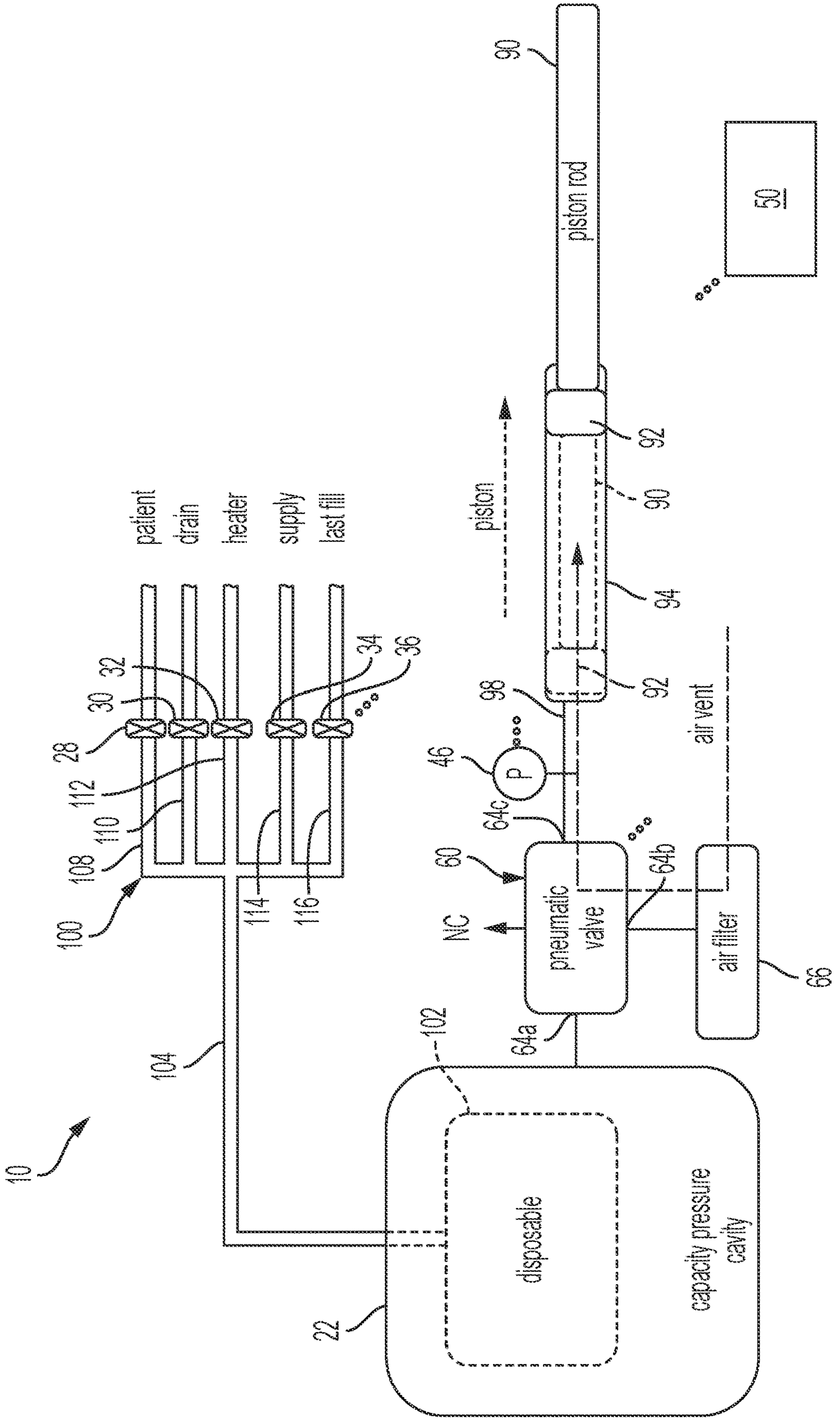
FIG. 6 is a schematic view illustrating a first step of one embodiment a positive pressure sequence using the pressure chamber APD system of the present disclosure.

Once container or bag 102 is full, the fluid is delivered to a desired destination. FIG. 6 illustrates via the piston arrow and motive fluid arrow, that in a first step to build positive pressure within pressure chamber 22, pressure chamber passage or port 64*a* is closed, while pneumatic vent passage or port 64*b* and cylinder passage or port 64*c* are opened. Piston 90 and head 92 are retracted within cylinder 94 to allow air to fill the cylinder through vent 66. All fluid valves 28 to 36 are closed.

Figure 7:
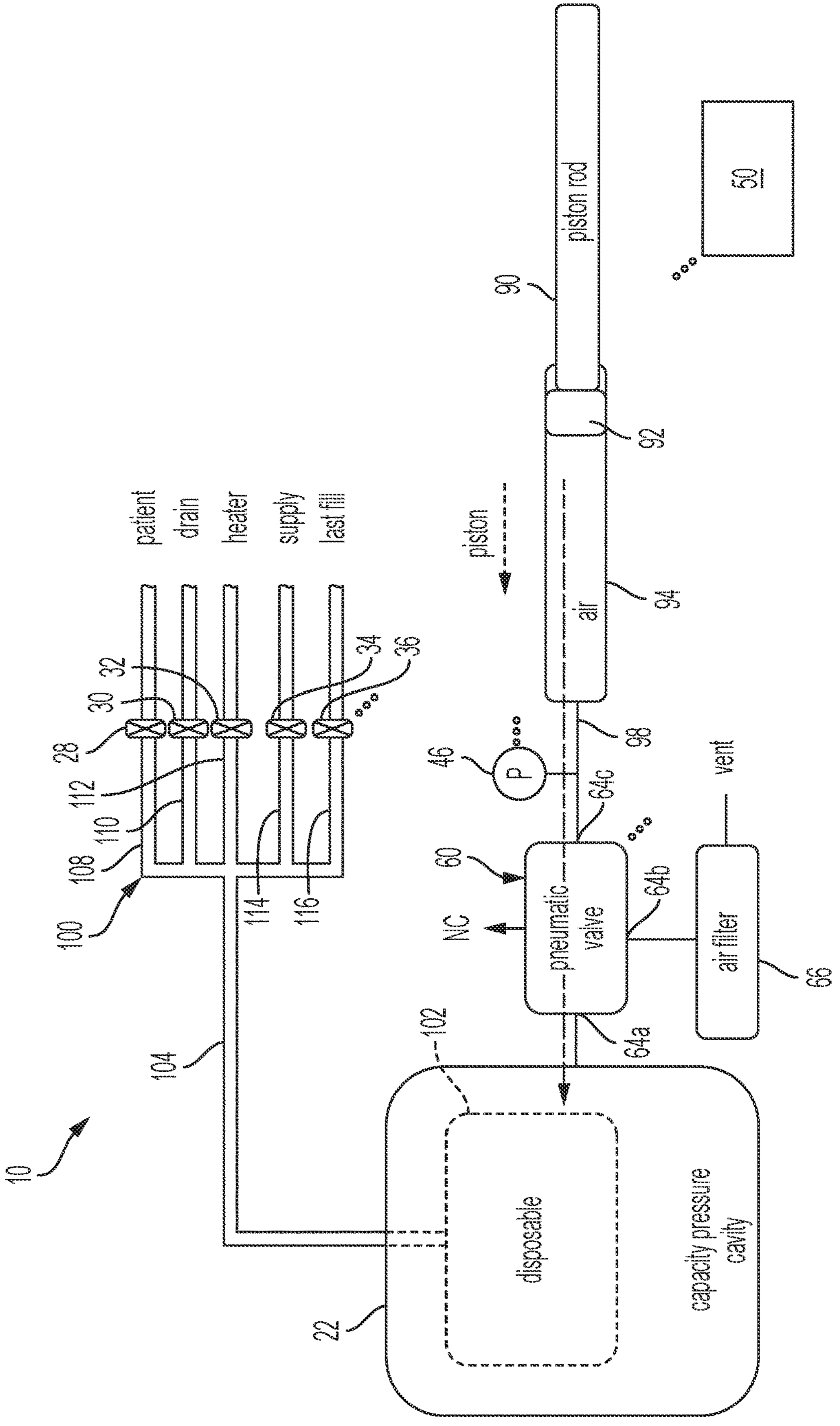
FIG. 7 is a schematic view illustrating a second step of one embodiment a positive pressure sequence using the pressure chamber APD system of the present disclosure.

Next as illustrated in FIG. 7 via the piston arrow and motive fluid arrow, vent port 64*b* is closed, while pressure chamber port 64*a* and cylinder passage or port 64*c* are opened. Piston 90 and head 92 are extended within cylinder 94 to build a certain amount of positive pressure in pressure chamber 22 as measured by pressure sensor 46.

The sequence just described between FIGS. 6 and 7 is repeated until a desired amount of positive pressure is built within pressure chamber 22 (e.g., +1.5 psig). When the desired positive starting pressure is built, a desired liquid destination valve is opened to expel a desired fluid (e.g., heated fresh via patient valve 28 to patient P, fresh supply to heater bag 122 via valve 32 or patient effluent to drain bag 120 via valve 30) from disposable flexible container or bag 102.

In one embodiment, the positive pressure in chamber 22 is relieved via the contraction of container or bag 102. The fluid valve is closed when pressure sensor 46, with passages or ports 64*a* and 64*c* opened and vent passage or port 64*b* closed, detects that the pressure has returned to 0 psig. The entire container 102 pump-out sequence, including the sequence described between FIGS. 6 and 7 and the fluid valve opening and closing just described, is then repeated to rebuild the starting positive pressure and to continue pumping from disposable container or bag 102, until there is no change in pressure as measured by pressure sensor 46 when the desired fluid valve is opened, indicating that container or bag 102 is full. That is, there is no more room within container or bag 102 to relieve the positive pressure.

In another embodiment, system 10 does not allow the pump-out pressure to fall to zero before rebuilding positive pressure within pressure chamber 22. This enables the pumping of fluid out of container or bag 102 to be performed on a more continuous basis. Here, as illustrated by the piston, motive fluid, and medical fluid arrows in FIG. 8, fluid valve 28, for example, is open so that fresh dialysis fluid flows to patient P. Valve 60 is placed in a state having pressure chamber passage or port 64*a* closed and vent and cylinder passages or ports 64*b* and 64*c* opened. Piston 90 and head 92 are retracted within cylinder 94 to draw motive fluid or air into the cylinder.

Figure 9:
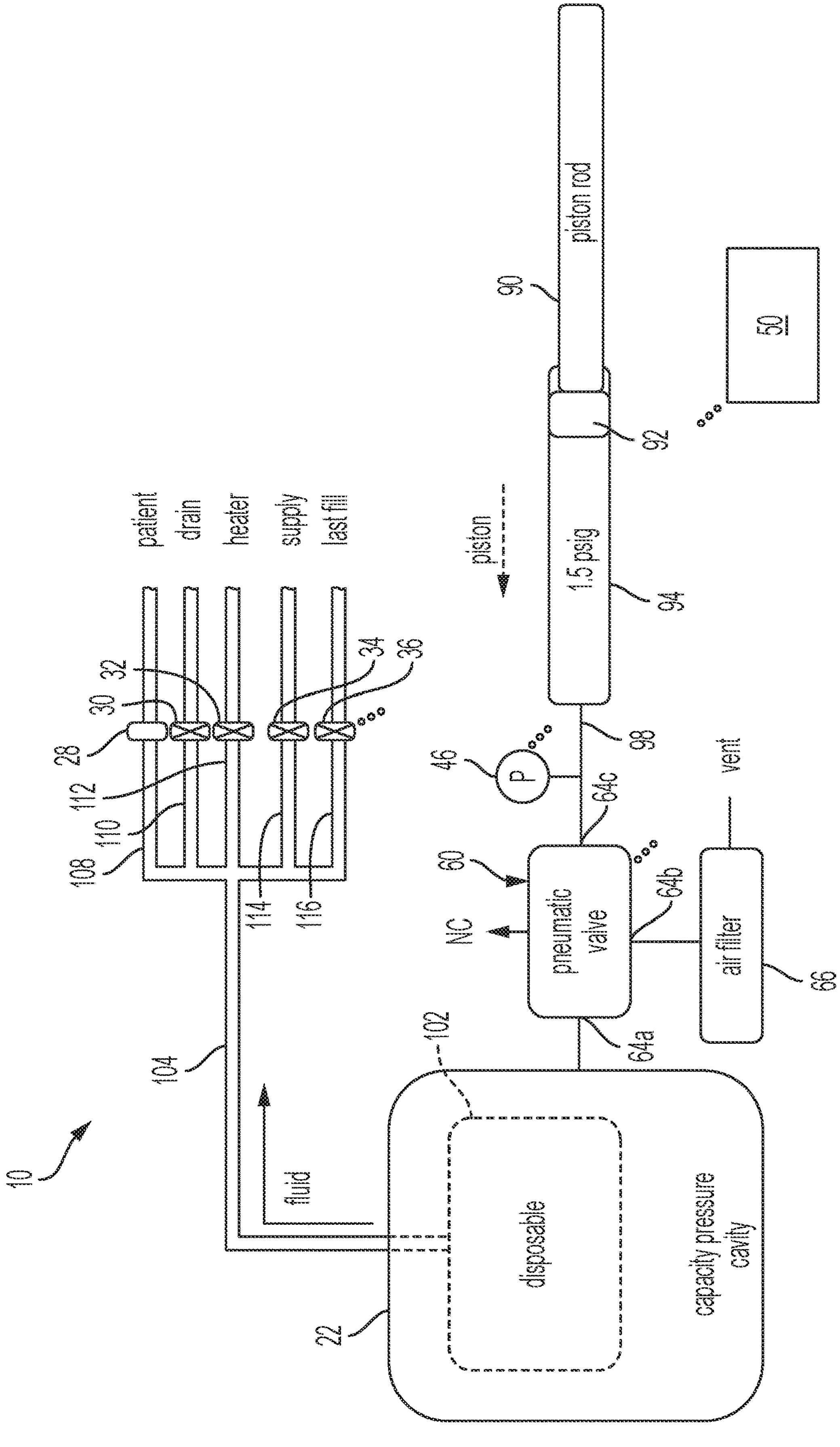
FIG. 9 is a schematic view illustrating a fourth step of one embodiment a positive pressure sequence using the pressure chamber APD system of the present disclosure.

In a next step illustrated in FIG. 9 with only piston and medical fluid arrows, all passageways or ports 64*a* to 64*c* of valve 60 are closed, while valve 28, for example, is open so that fresh dialysis fluid continues to flow to patient P. Piston 90 and head 92 are extended within cylinder 94 to pressurize air within the cylinder to the desired starting pressure as measured by pressure sensor 46, e.g., to 1.5 psig for pumping fresh dialysis fluid to patient P.

Figure 10:
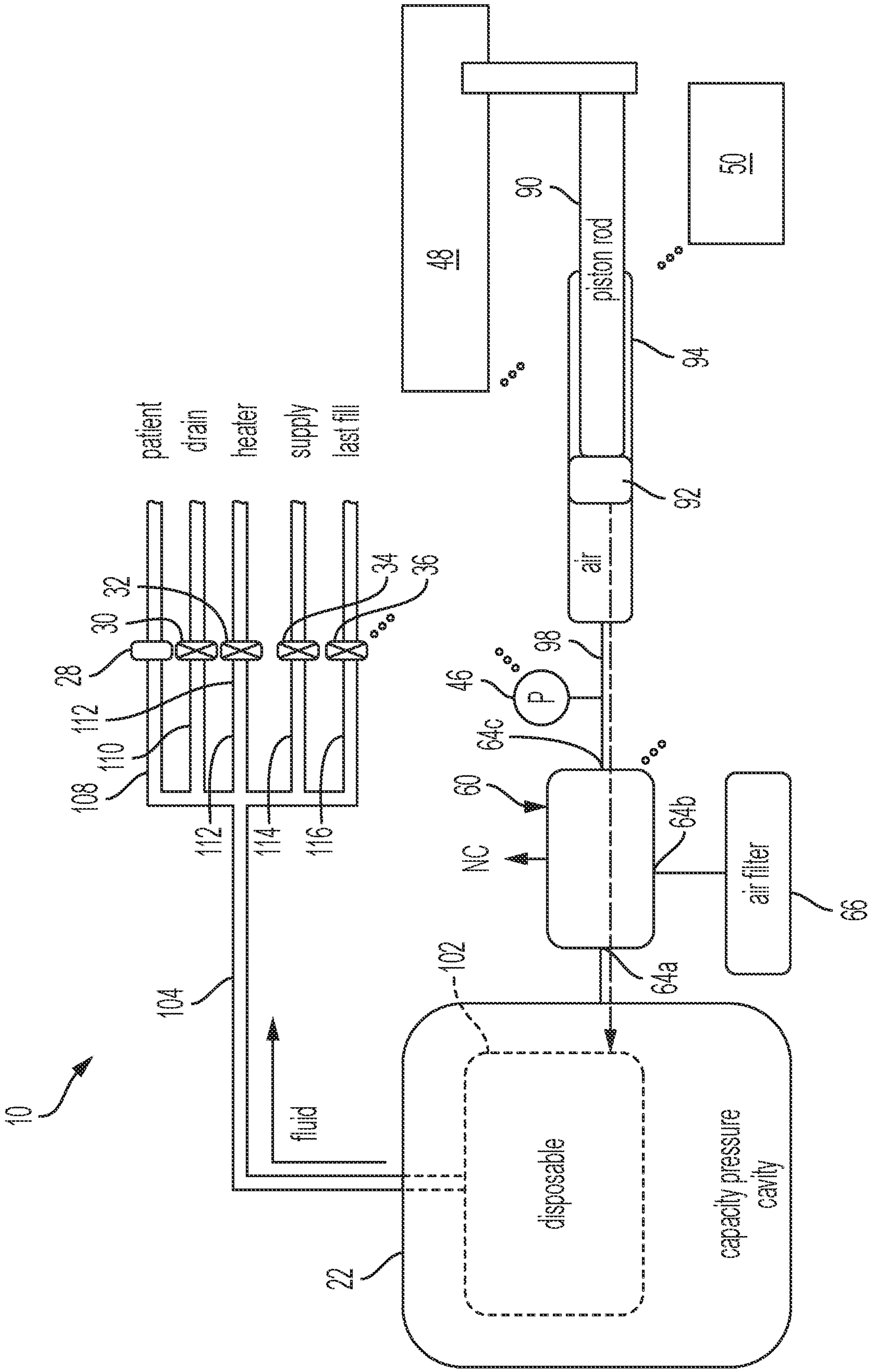
FIG. 10 is a schematic view illustrating a fifth step of one embodiment a positive pressure sequence using the pressure chamber APD system of the present disclosure.

In a next step illustrated in FIG. 10 by the motive fluid and medical fluid arrows, valve 28, for example, remains open so that fresh dialysis fluid continues to flow to patient P. Valve 60 is placed in a state having pressure chamber vent passage 64*b* closed and chamber and cylinder passages or ports 64*a* and 64*c* opened. Piston 90 and head 92 are maintained in the position achieved in FIG. 9 to rebuild the starting pressure. The rebuilt pressure, e.g., 1.5 psig, is then allowed to repressurize chamber 22 to continue to pump out dialysis fluid, but not above the set starting pressure.

Figure 8:
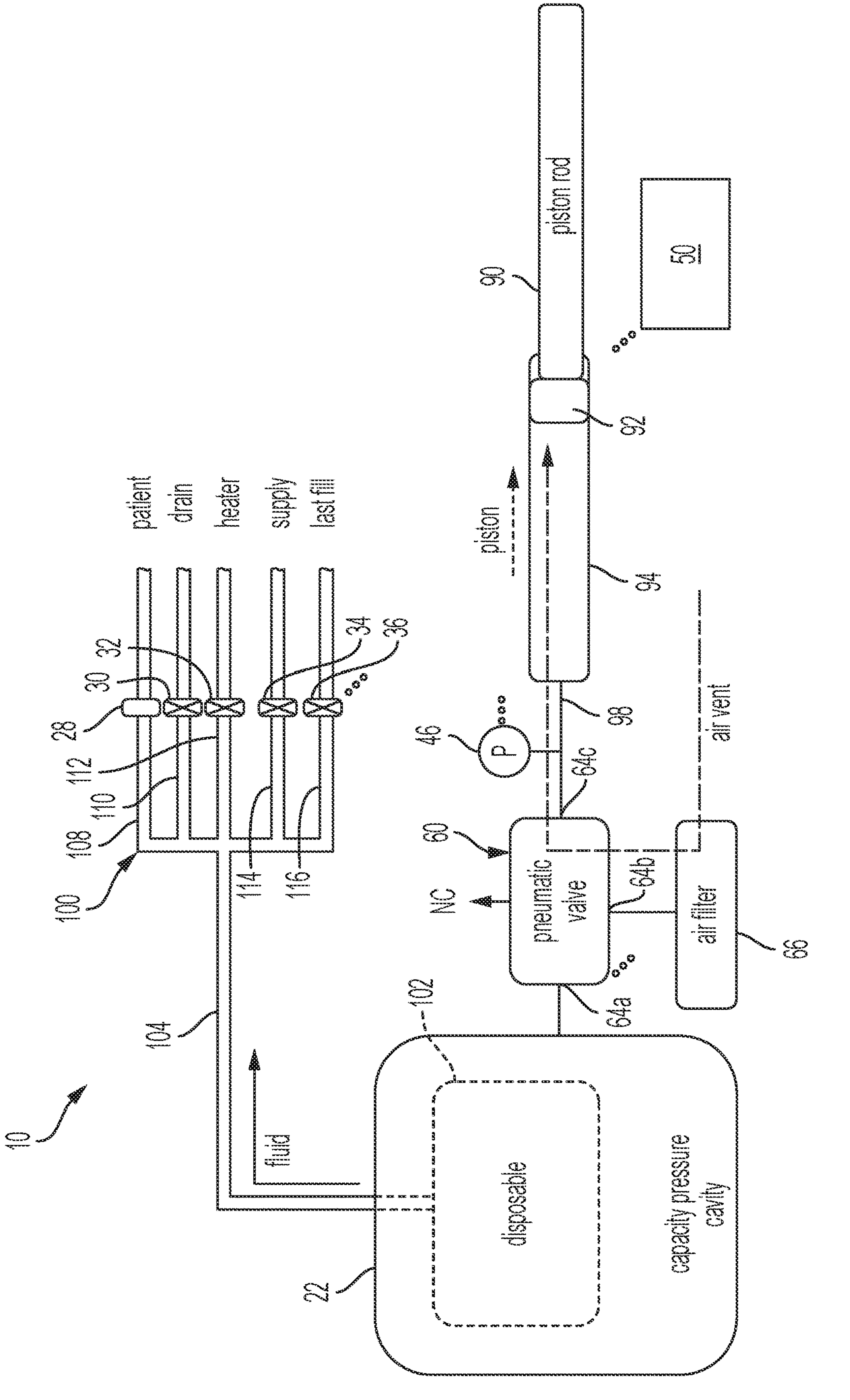
FIG. 8 is a schematic view illustrating a third step of one embodiment a positive pressure sequence using the pressure chamber APD system of the present disclosure.

The sequence in FIGS. 8 to 10 is repeated to create at least substantially continuous flow until pressure no longer drops within chamber 22, indicating that container or bag 102 is completely empty. That is, when piston 90 no longer needs to be moved to maintain a rebuilt pressure as sensed by pressure sensor 46, control unit 50 of system 10 determines that container or bag 102 is completely empty. It should be appreciated that rebuilding pressure prior to exhausting an existing driving pressure in chamber 22 may be performed in a similar manner using negative pressure to, for example, remove effluent from patient P in more continuous manner.

It should be also appreciated that in the illustrated embodiment, because the same pressure sensor 46 is used to measure pressure while both filling and emptying flexible container 102, drift in the pressure sensor over time is cancelled out. System 10 is accordingly robust from at least this standpoint.

To know how much fluid has been delivered to or from the disposable flexible container or bag, a rough estimate is provided by knowing and storing into memory the volume of the disposable bag and assuming the bag is completely filled from empty to full or completely emptied from full to empty. Alternatively, it may be estimated fairly accurately how much air is removed to container or bag 102 during priming of disposable set 100 and assumed that the air remains in the disposable set over the course of treatment. Here, the known volume of container or bag 102 less the estimated quantity of air is taken in memory 54 of control unit 50 as the volume of fluid completely filled from empty to full or completely emptied from full to empty. If a heater bag 122 is provided, system 10 may instead prime air initially in set 100 to the heater bag.

A more precise calculation is performed by adding volumes calculated from the sensed piston head displacements associated with building and rebuilding the negative and positive pressures, i.e., while passageways or ports 64*a* and 64*c* of valve 60 are open, storing the volumetric dimensions of cylinder 94, and assuming each of the fluids pumped to and from container or bag 102 to be incompressible. As discussed above, motor 72 may be provided with an encoder 76, which may be an incremental or absolute encoder. The encoder monitors the rotational position of the shaft of motor 72 and the numbers of turns it makes. That data in combination with the known translational distance per rotation of lead or ball screw 82 provides a precise distance that carriage 86, piston 90 and piston head 92 have moved. That distance multiplied by the area of, e.g., circular, cylinder 94 provides a precise displacement volume. Adding each displacement volume over a completed fill of container or bag 102 or a completed emptying of container or bag 102 results in a total volume of fluid filled or emptied.

FIG. 10 illustrates an alternative embodiment in which a potentiometer 48 is used instead of encoder 76. Potentiometer 48 outputs to control unit 50 as illustrated and directly measures the distance that carriage 86, piston 90 and piston head 92 have moved without having to know and rely on the geometry of lead or ball screw 82. A less expensive lead screw 82 may be used accordingly. The distance moved multiplied by the area of, e.g., circular, cylinder 94 again provides a precise displacement volume.

It is possible for system 10 of the present disclosure to encounter a situation in which chamber 22 is fully charged with pressure, e.g., to +1.5 psig, but container 102 is almost empty so the full +1.5 psig is not used to empty bag 102, e.g., the bag becomes completely empty at +1.0 psig. In such case, control unit 50 sees that the output from pressure sensor 46 has stopped falling and now remains constant at +1.0 psig. Control unit 50 from such detection determines that bag 102 is empty. Control unit 50 notes the position of piston head 92 at +1.0 psig and then causes piston head 92 to extend within cylinder 94 a distance until the pressure increases to +1.5 psig at which point the movement of piston head 92 is stopped and control unit 50 notes this second position of piston head 92. The difference in the two positions moving from +1.0 psig to +1.5 psig is assumed to result in the same volume, knowing the cross-sectional area of cylinder 94, as the volume of fluid delivered from +1.5 psig to +1.0 psig with piston head 92 held fixed. If there is not enough room in cylinder 94 to complete the pressure rebuild, it is contemplated for control unit 50 to cause: (i) cylinder 94 to vent via vent 66, (ii) piston head 92 to retract fully within cylinder 94, (iii) piston head 92 to be extended to a first noted position to achieve the original ending pressure, e.g., +1.0 psig, and (iv) piston head 92 to be further extended to a second noted position to achieve the original starting pressure, e.g., +1.5 psig. The difference between the two noted positions is assumed to result in the same volume, knowing the cross-sectional area of cylinder 94, as the volume of fluid delivered from +1.5 psig to +1.0 psig with piston head held fixed.

Alternatively or additionally (e.g., for confirmation) a look-up table may be provided, e.g., developed empirically as a part of the original software of system 10, or over time as system 10 is used, which correlates a particular pressure drop with a particular volume of fluid delivered. Further alternatively or additionally (e.g., for confirmation) an equation may be provided, e.g., developed empirically as a part of the original software of system 10, or over time as system 10 is used, which calculates a volume of fluid delivered knowing a particular pressure drop until bag 102 becomes empty.

In System 10, the same situation can occur in the negative pressure case in which bag 102 becomes completely full before fully relieving the negative pressure in the chamber.

For example, suppose bag 102 becomes full at −1.0 psig after starting from −1.5 psig. In such case, control unit 50 sees that the output from pressure sensor 46 has stopped falling and now remains constant at −1.0 psig. Control unit 50 from such detection determines that either (i) bag 102 is full or (ii) the patient is empty such that the current pressure can no longer remove fluid from the patient. Control unit 50 notes the position of piston head 92 at −1.0 psig and then causes piston head 92 to withdraw within cylinder 94 a distance until the negative pressure increases to −1.5 psig at which point the movement of piston head 92 is stopped and control unit 50 notes this second position of piston head 92. The difference in the two positions moving from −1.0 psig to −1.5 psig is assumed to result in the same volume, knowing the cross-sectional area of cylinder 94, as the volume of fluid received in bag 102 from −1.5 psig to −1.0 psig with piston head 92 held fixed. If there is not enough room in cylinder 94 to complete the pressure rebuild, it is contemplated for control unit 50 to cause: (i) cylinder 94 to vent via vent 66, (ii) piston head 92 to extend fully within cylinder 94, (iii) piston head 92 to be retracted to a first noted position to achieve the original ending pressure, e.g., −1.0 psig, and (iv) piston head 92 to be further retracted to a second noted position to achieve the original starting negative pressure, e.g., −1.5 psig. The difference between the two noted positions is assumed to result in the same volume, knowing the cross-sectional area of cylinder 94, as the volume of fluid delivered from −1.5 psig to −1.0 psig with piston head held fixed.

Alternatively or additionally (e.g., for confirmation) a look-up table may be provided, e.g., developed empirically as a part of the original software of system 10, or over time as system 10 is used, which correlates a particular pressure drop with a particular volume of fluid received in bag 102. Further alternatively or additionally (e.g., for confirmation) an equation may be provided, e.g., developed empirically as a part of the original software of system 10, or over time as system 10 is used, which calculates a volume of fluid received in bag 102 knowing a particular pressure drop until bag 102 becomes empty.

It is contemplated that control unit 50 be programmed to detect when the patient may be empty or close to empty when the negative pressure is sensed to remain constant as opposed to bag 102 becoming full. For instance, control unit 50 may be programmed to determine that a patient empty state is reached, as opposed to a bag being full state, after a certain volume of effluent has been removed from the patient, e.g., approaching an expected patient drain amount. Alternatively or additionally (e.g., for confirmation), control unit 50 may be programmed to determine that a patient empty state is reached, as opposed to a bag being full state, when the pressure reading stops changing and remains constant too soon after valve 60 is opened for a bag full state to possibly have been reached, e.g., within less than half of an expected amount of time.

In any case, when control unit 50 determines a patient empty (or near empty) state, it is contemplated that after determining the volume removed from the patient after the pressure stops changing as discussed above, control unit 50 with valve 60 closed causes piston head to retract to build negative pressure to a safe level, e.g., −1.5 psig, and to then open valve ports 64*a* and 64*c* to see if any additional effluent can be removed at this higher pressure. If the patient is completely empty, the raised negative pressure will not change. If the patient is close to empty, the raised negative pressure will be relieved until the patient becomes fully empty and the pressure stops changing. Control unit 50 then determines the additional volume removed from the patient and adds it to a total patient drain volume for the present fill, dwell and drain cycle.

Alternatively or additionally (e.g., for volume confirmation), systems 10 and 210 (discussed below) may include one or more load cell (not illustrated) that is located within lower clamshell portion 22*b* (FIG. 1), so that heater plate 42 rests on the one or more load cell. The one or more load cell outputs to control unit 50, which knowing the weight of plate 42 and bag 102 itself, may determine the total weight of a complete fill or empty of container or bag 102 by measuring the incremental weight due to the fluid filled or emptied.

Figure 11:
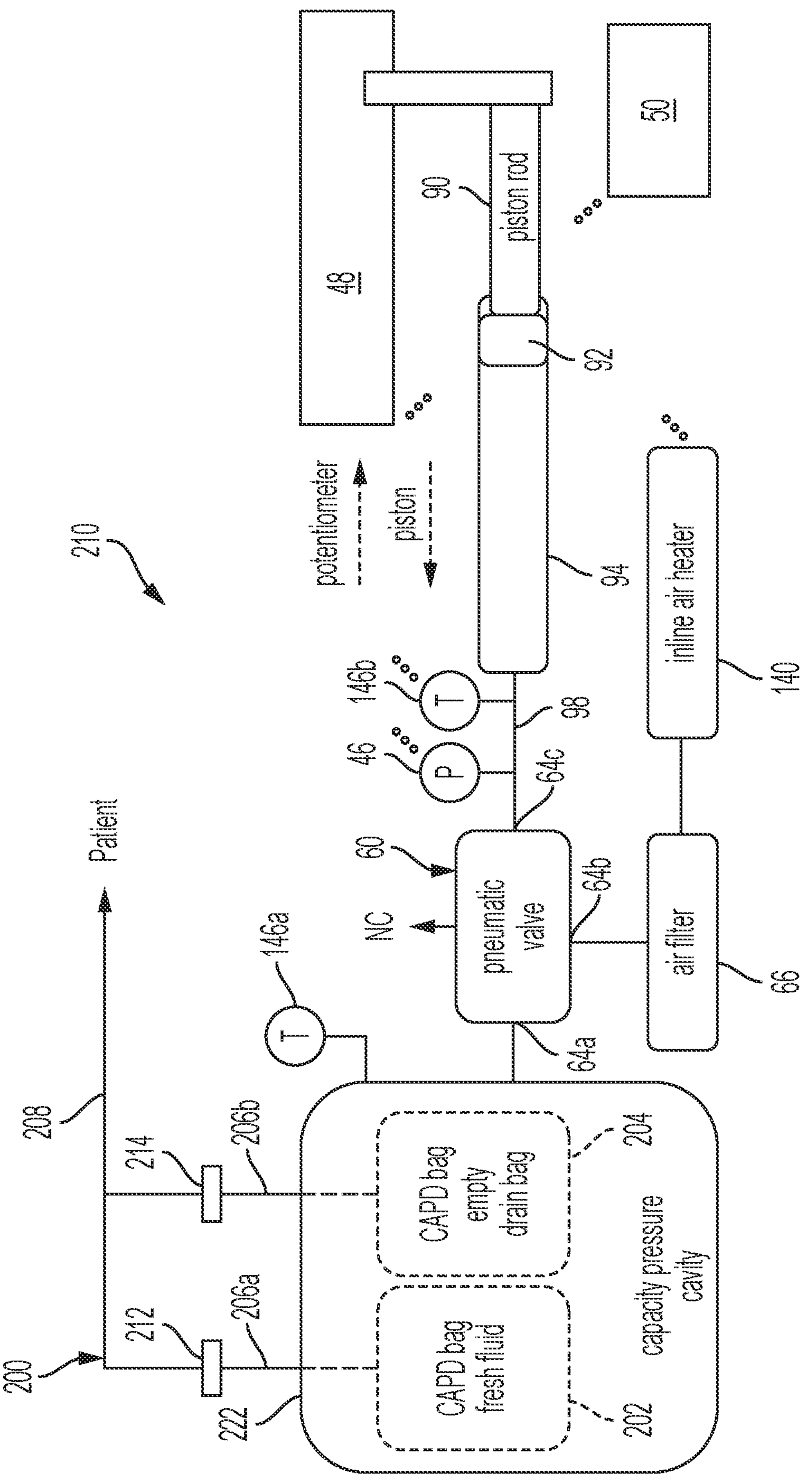
FIG. 11 is a schematic view illustrating one embodiment of a pressure chamber CAPD system of the present disclosure.

Referring now to FIG. 11, an alternative continuous ambulatory peritoneal dialysis system 210 is provided using an alternative pressure chamber housing 222, which in the illustrated embodiment is a rigid, e.g., clamshell, structure that accepts a fresh fluid disposable container 202 and a drain fluid disposable container 204, e.g., disposable flexible bags, of an alternative disposable set 200. Rigid container 222 may be made of plastic, such as, polyvinyl chloride ("PVC"), polyethylene ("PE") or polyurethane ("PU"), or of metal, such as stainless steel or aluminum. Rigid container 222 may be reusable or disposable. Disposable bags 202 and 204 may be made of a medically safe material such as PVC or a non-PVC material. Where chamber 222 is a clamshell chamber, a seal such as an o-ring seal (e.g., silicone) may be placed between the clamshell portions of chamber 222 to seal same when closed together, e.g., in a manner the same as or similar to that illustrated and described in connection with FIG. 1.

The clamshell portions may also seal about bag lines 206*a* and 206*b* leading from bags 202 and 204, respectively, in a manner the same as or similar to that illustrated and described in connection with FIG. 1. Bag lines 206*a* and 206*b* extend to a common patient line 208, which includes a connector at its distal end for connecting to a patient's transfer set. As illustrated in FIG. 11, bag lines 206*a* and 206*b* are positioned so as to operate with pinch valves 212 and 214, respectively, e.g., motorized pinch valves. Pinch valves 212 and 214 are alternatively manual clamps.

CAPD system 210 includes motive fluid or pneumatic valve 60 (e.g., three-way valve having ports 64*a* to 64*c*, pressure sensor 46, air filter 66, piston 90 (and associated motor, motor control devices, and encoder or potentiometer), piston head 92, piston cylinder 94 and pneumatic tube or line 98 including all of the structure, functionality and alternatives discussed above for system 10. CAPD system 210 and APD system 10 may additionally include one or more temperature sensor 146*a* and/or 146*b* outputting to control unit 50. In the illustrated embodiment, temperature sensor 146*a* is positioned and arranged to sense the temperature of air within chamber 222, while temperature sensor 146*b* is positioned and arranged to sense the temperature of air within pneumatic tube or line 98. CAPD system 210 and APD system 10 may additionally include an inline air heater 140 under control of control unit 50. The readout from temperature sensor 146*a* and/or 146*b* may be used as feedback by control unit 50 to actuate inline air heater 140 to try to match the air temperature inside pneumatic tube or line 98 with the air temperature within chamber 222. In an embodiment, control unit 50 attempts to maintain the temperature within chamber 222 and pneumatic tube or line 98 to be at body temperature or 37° C.

In an embodiment, control unit 50 of CAPD system 210 is programmed to allow the user to specify either a patient drain then fill (if initially full) or a patient fill, dwell, then drain (if initially empty). A patient drain is performed by pneumatically pulling effluent from the patient into drain fluid disposable container 204 according to any of the patient drain embodiments discussed above in connection with system 10, including (i) when drain container becomes full before an entire negative charge within chamber 222 is exhausted and (ii) when the patient becomes fully drained before an entire negative charge within chamber 222 is exhausted. A patient fill is performed by pushing fresh dialysis fluid from supply bag 202 to the patient according to any of the patient fill embodiments discussed above in connection with system 10, including when supply bag 202 is fully emptied before an entire positive charge within chamber 222 is exhausted. It is contemplated that CAPD system 210 may reduce patient fill and drain times by half versus gravity filling.

Control unit 50 monitors total fill and drain volumes over a specified period, e.g., twenty-four hours, calculates and reports to the patient an ultrafiltration ("UF") value for the specified period. Control unit 50 for system 210 may also include a transceiver and a wired or wireless connection to a network, e.g., the internet, for sending treatment data to, including daily UF data, and receiving prescription instructions from a doctor's or clinician's server interfacing with a doctor's or clinician's computer.

It should be understood that various changes and modifications to the presently preferred embodiments described herein will be apparent to those skilled in the art. For example, pneumatic valves may be used instead of electrically actuated pinch valves 28 to 36. In another example, stepper motor 72 and lead or ball screw 82 may be replaced with another type of linear actuator, such as a pneumatically or hydraulically actuated piston or with a linear motor. In a further example, three-way valve 60 may be replaced with a series of single direction valves. Moreover, other motive fluids, different than air may be used. Such changes and modifications can be made without departing from the spirit and scope of the present subject matter and without diminishing its intended advantages. It is therefore intended that such changes and modifications be covered by the appended claims.

The invention is claimed as follows:

1. A peritoneal dialysis system comprising:

a pressure chamber;

a disposable set including a flexible container located within the pressure chamber, at least one source line and at least one destination line;

a motive fluid pressurization device;

a motive fluid pressure sensor; and a control unit in operable communication with the motive fluid pressurization device and the motive fluid pressure sensor, the control unit configured to (i) pressurize the pressure chamber on the outside of the flexible container to a desired positive or negative motive fluid pressure used to push fluid out of the flexible container through one of the at least one destination line or pull fluid into the flexible container through one of the at least one source line, respectively, and (ii) repeat (i) until a motive fluid pressure read by the motive fluid pressure sensor becomes or remains at least substantially constant when it is attempted to push fluid out of the flexible container or pull fluid into the flexible container, indicating that the flexible container is empty or full, respectively.

2. The peritoneal dialysis system of claim 1, wherein the pressure chamber is reusable and is configured to open to accept the flexible container and to close to seal around a common line extending from the flexible container.

3. The peritoneal dialysis system of claim 1, wherein the pressure chamber is disposable and sealed to a common line extending from the flexible container.

4. The peritoneal dialysis system of claim 1, wherein the at least one source line includes at least one supply line connected to a supply of fresh peritoneal dialysis fluid and a patient line for removing used peritoneal dialysis fluid, and the at least one destination line includes the patient line for delivering fresh peritoneal dialysis fluid and a drain line for removing used peritoneal dialysis fluid.

5. The peritoneal dialysis system of claim 1, wherein the pressure chamber includes a fluid heater positioned to heat fluid within the flexible container.

6. The peritoneal dialysis system of claim 1, wherein the at least one source line and the at least one destination line include a heater line for extending to a heating container for heating fresh peritoneal dialysis fluid.

7. The peritoneal dialysis system of claim 1, wherein the motive fluid pressurization device includes a motive fluid cylinder, a piston located within the motive fluid cylinder, and a linear actuator configured to extend and retract the piston.

8. The peritoneal dialysis system of claim 7, which includes at least one motive fluid valve for opening and closing a pressure chamber passage and a vent passage, and wherein during (i) and (ii) the control unit is configured to perform a negative pressure sequence in which (a) the pressure chamber passage is closed and the vent passage is opened while the piston is extended within the motive fluid cylinder to push motive fluid out of the cylinder, after which (b) the pressure chamber passage is opened and the vent passage is closed while the piston is retracted to pull motive fluid from the pressure chamber into the cylinder to increase the negative pressure within the pressure chamber.

9. The peritoneal dialysis system of claim 8, which includes a fluid valve associated with each of the at least one source lines, and wherein the control unit is configured to open a desired one of the fluid valves when the desired negative motive fluid pressure is reached via the negative pressure sequence.

10. The peritoneal dialysis system of claim 9, wherein the fluid valve includes a source line pinch valve.

11. The peritoneal dialysis system of claim 7, which includes at least one motive fluid valve for opening and closing a pressure chamber passage and a vent passage, and wherein during (i) and (ii) the control unit is configured to perform a positive pressure sequence in which (a) the pressure chamber passage is closed and the vent passage is opened while the piston is retracted within the motive fluid cylinder to pull motive fluid into the cylinder, after which (b) the pressure chamber passage is opened and the vent passage is closed while the piston is extended to push motive fluid from cylinder into the pressure chamber to increase the positive pressure within the pressure chamber.

12. The peritoneal dialysis system of claim 11, which includes a fluid valve associated with each of the at least one destination lines, and wherein the control unit is configured to open a desired one of the fluid valves when the desired positive motive fluid pressure is reached via the positive pressure sequence.

13. The peritoneal dialysis system of claim 12, wherein the fluid valve includes a destination line pinch valve.

14. The peritoneal dialysis system of claim 7, wherein the linear actuator includes a ball or lead screw driven by a motor under control of the control unit.

15. The peritoneal dialysis system of claim 7, which includes a feedback mechanism outputting to the control unit to enable the control unit to determine how far the linear actuator has extended or retracted the piston.

* * * * *